United States Patent [19]

Satoh

[11] Patent Number: 5,104,999

[45] Date of Patent: Apr. 14, 1992

[54] METHOD OF PURIFICATION OF ALKOXYSILANES

[75] Inventor: Norio Satoh, Ohta, Japan

[73] Assignee: Toshiba Silicone Co., Ltd., Japan

[21] Appl. No.: 693,487

[22] Filed: Apr. 30, 1991

[30] Foreign Application Priority Data

May 18, 1990 [JP] Japan .................................. 2-128577

[51] Int. Cl.$^5$ .............................................. C07F 7/20
[52] U.S. Cl. .................................................... 556/466
[58] Field of Search ......................................... 556/466

[56] References Cited

U.S. PATENT DOCUMENTS

| 4,774,347 | 9/1988 | Marko et al. | 556/466 |
| 4,956,486 | 9/1990 | Marko et al. | 556/466 |
| 4,962,221 | 10/1990 | Huntress et al. | 556/466 X |

FOREIGN PATENT DOCUMENTS

| 0235887 | 9/1990 | Japan | 556/466 |
| 0880211 | 10/1961 | United Kingdom | 556/466 |
| 0933491 | 8/1963 | United Kingdom | 556/466 |

Primary Examiner—Paul F. Shaver

[57] ABSTRACT

A halide-containing alkoxysilane is brought into contact with a zinc metal or an organic zinc compound to remove the halide from the alkoxysilane, simply and effectively, to thereby provide a purified alkoxysilane.

15 Claims, No Drawings

METHOD OF PURIFICATION OF ALKOXYSILANES

The present application claims the priority of Japanese Patent Application Serial No. 02-128577 filed on May 18, 1990.

BACKGROUND OF THE INVENTION

The present invention relates to a method of decreasing the content of impurities in alkoxysilanes.

In alkoxysilanes used as industrial materials in the technical field of semiconductors, it has been found that a small amount of halides such as organic halide compounds present therein as impurities often corrode semiconductor substrates and cause problems in semiconductor materials.

As a method of reducing the content of impurities in alkoxysilanes, for example, JP-A-63-238091 discloses a method of using a metal alcoholate in an amount more than the chemical equivalent amount of the chloride compound to be contained in an alkoxysilane as an impurity. (The term "JP-A" as used herein means an "unexamined published Japanese patent application".) In this method, however, removal of organic halide compounds is difficult. On the other hand, JP-A-63-77887 describes a method of purifying an organic silicon compound by bringing the compound into contact with an organic magnesium compound. However, industrial preparation of organic magnesium compounds used in this method is difficult. Additionally, when the method is applied to purification of alkoxysilanes, the alkoxy group reacts with the organic residue of the organic magnesium compound and thereby lowers the yield of the alkoxysilane product. Thus, this method has various problems.

SUMMARY OF THE INVENTION

The object of the present invention is to provide a method of simply and effectively removing halide impurities from alkoxysilanes to thereby purify alkoxysilanes.

The present invention is based o the discovery that zinc metal and/or organic zinc compounds are effective for removing halide impurities from alkoxysilanes. On the basis of the finding, he has achieved the present invention.

DETAILED DESCRIPTION OF THE INVENTION

Specifically, the present invention provides a method of removing halides from an alkoxysilane containing halide(s) in which the halide-containing alkoxysilane is brought into contact with a zinc metal and/or organic zinc compound(s) and thereafter the alkoxysilane and the zinc metal and/or organic zinc compound are separated.

Alkoxysilanes purified by the method of the present invention include monoalkoxysilanes such as trimethylmethoxysilane, trimethylethoxysilane, triethyl-methoxysilane, trimethylisopropoxysilane, trimethyl-butoxysilane, triphenylmethoxysilane, dimethyl-t-butylmethoxysilane, triphenylethoxysilane, and dimethyl-phenylmethoxysilane; dialkoxysilanes such as dimethyl-dimethoxysilane, dimethyldiethoxysilane, diethyl-dimethoxysilane, diphenyldimethoxysilane, diphenyl-diethoxysilane, methylphenyldimethoxysilane and methyl-phenyldiethoxysilane; trialkoxysilanes such as methyl-trimethoxysilane, methyltriethoxysilane, ethyltri-methoxysilane, phenyltrimethoxysilane and phenyltri-ethoxysilane; as well as tetraalkoxysilanes such as tetramethoxysilane, tetraethoxysilane and tetraiso-propoxysilane.

Examples of halides which are removed from the above-mentioned alkoxysilanes by the method of the present invention include organic halide compounds such as methyl chloride, methyl bromide, chlorobenzene, bromobenzene, chlorobiphenyl and bromobiphenyl, as well as hydrogen chloride and other chlorosilane compounds. However, suitable halides for use in the method of this invention are not restricted to those listed above but include any halide which may be present in alkoxysilanes.

As the zinc metal used in the method of the present invention, a powdery one having a large surface area is preferred. Examples of organic zinc compounds usable in the method of the present invention include alcoholate compounds such as dimethoxy zinc, diethoxy zinc and di-n-propoxy zinc, as well as carbonate compounds such as zinc octenoate and zinc caprylate.

These may be used singly or in combination of two or more of them.

Additionally, a porous substance such as active charcoal or alumina and a metal alcoholate may be used in the method of the present invention along with the above-mentioned zinc metal and/or organic zinc compound(s), provided that they do not adversely affect the method of the present invention.

In carrying out the method of the present invention, the amount of the zinc metal and/or organic zinc compound(s) to be used is preferably from 1 to 100 times, more preferably from 5 to 50 times, the amount of organic halide impurities in the alkoxysilane to be purified by the method of the invention. The length of contact time between the alkoxysilane to be purified and the zinc metal and/or organic zinc compound(s) in the method of the invention may be varied, depending upon the amount of organic halide compounds and the amount of zinc metal and/or organic metal compound(s). In general, it is desirably approximately from 3 to 10 hours.

The temperature at which contact between the alkoxysilane and the zinc metal and/or organic metal compound is effected may be within the range of from 50° to 250° C. In general, however, the method may effectively be carried out at the reflux temperature of an alkoxysilane to be purified or a temperature lower than the reflux temperature.

After treatment of the alkoxysilane with the zinc metal and/or organic metal compound is complete, the resulting reaction mixture is, either directly or after filtered, subjected to distillation at normal pressure or under reduced pressure by methods known in the art to thereby isolate the purified alkoxysilane.

EXAMPLES OF THE INVENTION

Next, the present invention will be explained in more detail by way of the following examples, which, however, are not intended to restrict the scope of the present invention. In the following examples, quantitative determination impurities was effected by fluorescent X-ray method or oxidative decomposition coulometric titration method (Chlorine Analysis Device, TSX-15 Type, manufactured by Mitsubishi Kasei Corp., Japan). Additionally, the electroconductivity of the purified product was also determined.

In the following examples, quantitative determination of impurities was effected by fluorescent X-ray method or oxidative decomposition coulometric titration method (Chlorine Analysis Device, TSX-15 Type, manufactured by Mitsubishi Kasei Corp., Japan). Additionally, the electroconductivity of the purified product was also determined.

EXAMPLE 1

100 g of methyltrimethoxysilane containing impurities, which had been determined to have a chlorine content of 114 ppm by oxidative decomposition coulometric titration method and an electroconductivity of 15.8 μS/cm, was put in a flask, and 2 g of a powdery zinc metal was added thereto. Then, the mixture was heat-treated at the reflux temperature of methyltrimethoxy-silane (about 103° C.) for 4 hours at normal pressure and thereafter subjected to distillation to obtain 95 g of methyltrimethoxysilane. The product had a chlorine content of 1 ppm, as determined by oxidative decomposition coulometric titration method, and had an electroconductivity of 0.3 μS/cm.

COMPARATIVE EXAMPLE 1

100 g of the same impurities-containing methyltrimethoxysilane as that used in Example 1 was fed into the same device as that also used in Example 1, and this was heat-treated at the reflux temperature (about 103° C.) for 4 hours at normal pressure with addition of nothing thereto and thereafter subjected to re-distillation to obtain 96 g of methyltrimethoxysilane. The product had a chlorine content of 76 ppm, as determined by oxidative decomposition coulometric titration method, and had an electroconductivity of 8.7 μS/cm.

COMPARATIVE EXAMPLE 2

100 g of the same impurities-containing methyltrimethoxysilane as that used in Example 1 was fed into the same device as that also used in Example 1, and this was treated in the same manner as in Example 1 except that 2 g of sodium methylate was added thereto, to obtain 94 g of methyltrimethoxysilane.

The product thus obtained had a chlorine content of 65 ppm, as determined by oxidative decomposition coulometric titration method, and had an electro-conductivity of 8.5 μS/cm.

COMPARATIVE EXAMPLE 3

100 g of the same impurities-containing methyltrimethoxysilane as that used in Example 1 was fed into the same device as that also used in Example 1, and this was treated in the same manner as in Example 1 except that 2 g of a powdery magnesium metal was added thereto, to obtain 95 g of methyltrimethoxysilane.

The product thus obtained had a chlorine content of 70 ppm, as determined by oxidative decomposition coulometric titration method, and an electroconductivity of 8.6 μS/cm.

EXAMPLE 2

100 g of methyltriethoxysilane, which had been determined to have a chlorine content of 13 ppm by oxidative decomposition coulometric titration method, was put in a flask, and 10 g of zinc octenoate having a zinc content of 8% was added thereto. Then, the mixture was heat-treated for 5 hours at 80° C. at normal pressure and thereafter directly subjected to distillation to obtain 90 g of methyltriethoxysilane. The methyltriethoxysilane thus purified was ascertained to have a reduced chlorine content of 1 ppm by oxidative decomposition coulometric titration method.

EXAMPLE 3

100 g of dimethyldiethoxysilane, which had been determined to have a bromine content of 116 ppm by fluorescent X-ray analysis method, was put in a flask, and 2 g of a powdery zinc metal and 1 g of an active charcoal were added thereto. Then, the mixture was heat-treated at the reflux temperature of dimethyle-diethoxysilane (about 115° C.) for 5 hours at normal pressure and thereafter filtered through a filter paper and subjected to distillation at normal pressure, to obtain 90 g of dimethyldiethoxysilane. No bromine content was detected in the thus purified product, by fluorescent X-ray analysis method.

What is claimed is:

1. A method of removing organic halides from alkoxysilanes, comprising treating an organic halide-containing alkoxysilane with sinc metal or organic zinc compound and thereafter isolating the treated alkoxysilane.

2. The method of claim 1 wherein the zinc metal is powdery.

3. The method of claim 1 wherein the organic zinc compound is selected from the group consisting of zinc alcoholate compounds and zinc carbonate compounds.

4. The method of claim 1 wherein the organic zinc compound is selected from the group consisting of dimethoxy zinc, diethoxy zinc, di-n-propoxy zinc, zinc octenoate and zinc caprylate.

5. The method of claim 1 wherein the amount of the zinc metal or organic zinc compound is from 1 to 100 times the amount of organic halide to be removed from the alkoxysilane.

6. The method of claim 1 wherein the alkoxysilane and the zinc metal or organic zinc compound(s) are in contact for approximately from 3 to 10 hours.

7. The method of claim 1 wherein the alkoxysilane is treated with the zinc metal or organic zinc compound(s) at the reflux temperature of the alkoxysilane or lower, the temperature being within the range of from 50° to 250° C.

8. The method of claim 1 wherein the treated alkoxysilane is isolated by distillation.

9. A method of removing halides from alkoxysilanes, comprising treating a halide-containing alkoxysilane with an organic zinc compound selected from the group consisting of zinc alcoholate compounds and zinc carbonate compounds and thereafter isolation the treated alkoxysilane wherein the halide present in the alkoxysilane is an organic halide compound, hydrogen chloride or a chlorosilane compound.

10. The method of claim 1 wherein the alkoxysilane is selected from the group consisting of monoalkoxysilanes, dialkoxysilanes, trialkoxysilanes and tetraalkoxysilanes.

11. The method of claim 1 wherein the alkoxysilane is selected from the group consisting of trimethylmethoxy-silane, trimethylethoxysilane, triethylmethoxysilane, trimethylisopropoxysilane, trimethylbutoxysilane, tri-phenylmethoxysilane, dimethyl-t-butylmethoxysilane, tri-phenylethoxysilane, dimethylphenylmethoxysilane, di-methyldimethoxysilane, dimethyldiethoxysilane, diethyl-dimethoxysilane, diphenyldimethoxysilane, diphenyl-diethoxysilane, methylphenyldimethoxysilane, methyl-phenyldiethoxysilane, methyltrimethoxysilane, methyl-triethoxysilane, ethyltrimethoxysilane, phenyltri-methoxysilane, phenyltriethoxysilane, tetramethoxysilane, tetraethoxysilane and tetraisopropoxysilane.

12. The method of claim 1 in which active charcoal or alumina is added along with the zinc metal or organic zinc compound.

13. The method of claim 12 in which the treating is conducted at the reflux temperature of the alkoxysilane.

14. The method of claim 1 in which the organic halide to be removed is methyl chloride, methyl bromide, chlorobenzene, bromobenzene, chlorobiphenyl or bromobiphenyl.

15. The method of claim 14 in which the organic halide is methyl chloride.

* * * * *